United States Patent [19]

Heiliger et al.

[11] Patent Number: 5,760,101
[45] Date of Patent: Jun. 2, 1998

[54] DERIVATIVES OF AROMATIC CARBOXYLIC ACIDS FROM AROMATIC CARBOXYLIC ACID ANHYDRIDES AND HYDROXY(METH) ACRYLATES AND FORMULATIONS THEREOF

[75] Inventors: Ludger Heiliger, Leverkusen; Wolfgang Podszun, Köln; Werner Finger, Neuss, all of Germany

[73] Assignee: Heraeus Kulzer GmbH, Hanau, Germany

[21] Appl. No.: 813,496

[22] Filed: Mar. 7, 1997

Related U.S. Application Data

[63] Continuation of PCT/EP96/02986, Jul. 8, 1996.

[30] Foreign Application Priority Data

Jul. 10, 1995 [DE] Germany ............... 195 25 031.1

[51] Int. Cl.⁶ ............... A61C 5/00; C08G 63/52
[52] U.S. Cl. ............... 523/115; 523/116; 523/118; 528/272; 528/296; 528/306; 106/35; 433/228.1
[58] Field of Search ............... 523/115, 116; 528/272, 301, 296, 306

[56] References Cited

U.S. PATENT DOCUMENTS

| 4,148,988 | 4/1979 | Masuhara et al. | 526/318 |
|---|---|---|---|
| 4,323,696 | 4/1982 | Schmitz-Josten et al. | 526/282 |
| 4,400,159 | 8/1983 | Orlowski et al. | 526/116 |
| 4,437,836 | 3/1984 | Schmitz-Josten et al. | 433/199 |
| 4,879,402 | 11/1989 | Reiners et al. | 526/301 |
| 4,952,614 | 8/1990 | Reiners et al. | 523/115 |
| 5,241,081 | 8/1993 | Müller et al. | 549/232 |
| 5,294,646 | 3/1994 | Müller et al. | 523/120 |
| 5,658,963 | 8/1997 | Qian et al. | 523/116 |

FOREIGN PATENT DOCUMENTS

| 023 686 | 2/1981 | European Pat. Off. . |
|---|---|---|
| 254 950 | 2/1988 | European Pat. Off. . |
| 471 252 | 8/1991 | European Pat. Off. . |
| 31 35 113 | 3/1983 | Germany . |
| 37 03 080 | 1/1988 | Germany . |
| 37 03 120 | 1/1988 | Germany . |
| 37 03 130 | 1/1988 | Germany . |
| 41 41 174 | 6/1992 | Germany . |

OTHER PUBLICATIONS

Patent Abstracts of Japan, vol. 8, No. 3 (C–203) for JP 58–173175, Oct. 12, 1983.
Derwent Abstract, AN 82–29376E for JP 57–038750, Mar. 3, 1982.

Primary Examiner—Tae Yoon
Attorney, Agent, or Firm—Frishauf, Holtz, Goodman, Langer & Chick, P.C.

[57] ABSTRACT

A condensation product of a hydroxy(meth)acrylate compound corresponding to the formula $$\begin{array}{c} R_1 \\ \diagup \\ \diagup \diagdown \\ C \\ \| \\ O \end{array} O-A \begin{array}{c} OH \\ \diagup \\ \diagdown \\ OH \end{array} \quad (I)$$

in which $R_1$ is hydrogen or methyl, A is a trivalent aliphatic residue with 3 to 15 C-atoms which is unsubstituted or substituted with OH groups and optionally contains up to 5 ether bridges, and an aromatic carboxylic acid anhydrides compound of the formula (II) or an aromatic carboxylic acid anhydride chloride compound of the formula (II)

$$\left( O \diagdown \begin{array}{c} O \\ \| \\ \diagup \\ \diagdown \\ \| \\ O \end{array} Ar \right)_n \left( Ar \begin{array}{c} Cl \\ \diagdown \\ \diagup \\ O \end{array} \right)_m \quad (II)$$

in which Ar is a in which Ar is a benzene ring or a naphthalene ring, n is 1 or 2, and m is 0, 1 or 2. The condensation product has a molar mass of 300 and to 10,000 daltons. The condensation product is useful as an adhesive to bond dental filling materials to teeth.

7 Claims, No Drawings

DERIVATIVES OF AROMATIC CARBOXYLIC ACIDS FROM AROMATIC CARBOXYLIC ACID ANHYDRIDES AND HYDROXY(METH) ACRYLATES AND FORMULATIONS THEREOF

CROSS REFERENCE TO RELATED APPLICATION

This application is a Continuation Application of International Application No. PCT/EP96/02986 filed Jul. 8, 1996, the entire contents of which are incorporated by reference herein.

BACKGROUND OF THE INVENTION

FIELD OF THE INVENTION

The present invention relates to new oligomeric condensation products from aromatic carboxylic acid anhydrides or aromatic carboxylic acid anhydride chlorides and hydroxyalkyl(meth)acrylates, respectively, as well as formulations of these compounds, preferably for use as adhesives in dental technology.

BACKGROUND INFORMATION

A specific, serious problem in the field of conservative dentistry is to form a durable, gap-free bond of synthetic filling materials with the hard substance of the tooth (dentine and tooth enamel). In the dental field, curing materials are used as filling materials for dental restoration. As curing materials, acrylic resin-based materials, which can be cured by radical polymerization, are generally preferred. A disadvantage of these materials is that they shrink during the curing process and thus contribute to the formation of gaps. The polymeric fillings have the additional disadvantage that their adhesion to dentine is poor.

In order to improve bonding with the hard substance of the tooth, so-called adhesion promoters or adhesives, respectively, can be used. As an active component of such adhesives for fillings in the dental field, methacryloyloxyalkyl derivatives of aromatic carboxylic acids are used, for example. Thus, in U.S. Pat. No. 4,148,988, for example, mixtures of trimellitic acid-4-methacryloyloxyethyl ester (4-MET) or trimellitic acid anhydride-4-methacryloyloxyethyl ester (4-META) with ethylenically unsaturated monomers and radical initiators are described.

A commercial product synthesized from 4-META (Superbond from Sun Medical Co., Ltd., Moriyama, Shiga, Japan) must be mixed with methyl methacrylate (MMA), polymethyl methacrylate (PMMA) and partially oxidized tri-n-butyl-borane (TBB) in order to obtain the ready-to-apply form (MMA-4-META-TBB resin).

In EP 0 471 252 B1, N-alkyl-N-(meth)acryloyloxyalkylcarboxamides of aromatic carboxylic acids and carboxylic acid anhydrides are proposed as components for adhesives. Significantly simplified application formulas result for these (meth)acryloyloxyalkyl derivatives.

A disadvantage of the known (meth)acryloyloxyalkyl derivatives of aromatic carboxylic acids is their relatively poor polymerizability. This results in several serious disadvantages. For example, the curing might be incomplete which may result in monomer residues and requires using drastic conditions when curing, for example, prolonged irradiation.

SUMMARY OF THE INVENTION

It has now been discovered that with the aid of the new oligomeric condensation products from aromatic carboxylic acid anhydrides or aromatic carboxylic acid anhydride chlorides and polyvalent hydroxyalkyl(meth)acrylates, respectively, adhesives can be formulated, preferably such which are suitable for treating the hard substance of a tooth, which feature a significantly enhanced polymerizability.

Oligomeric condensation products from aromatic carboxylic acid anhydrides or aromatic carboxylic acid anhydride chlorides and polyvalent hydroxyalkyl(meth)acrylates, respectively, refer to those which can be derived of the following monomers (I) and (II) through condensation reactions:

The monomers correspond to the following formula (I):

in which $R_1$ refers to hydrogen or methyl,

A refers to a trivalent aliphatic residue with 3 to 15 C-atoms which may be substituted with OH groups and may contain up to 5 ether bridges, and to the following formula (II):

in which

Ar stands for a benzene ring or a naphthalene ring, n refers to 1 or 2, and m is 0, 1 or 2.

The aliphatic residue A in monomer (I) may be linear, branched or cyclic. Particularly preferred are linear or branched residues. Particularly well-sui-ted aliphatic residues A are, for example, the following:

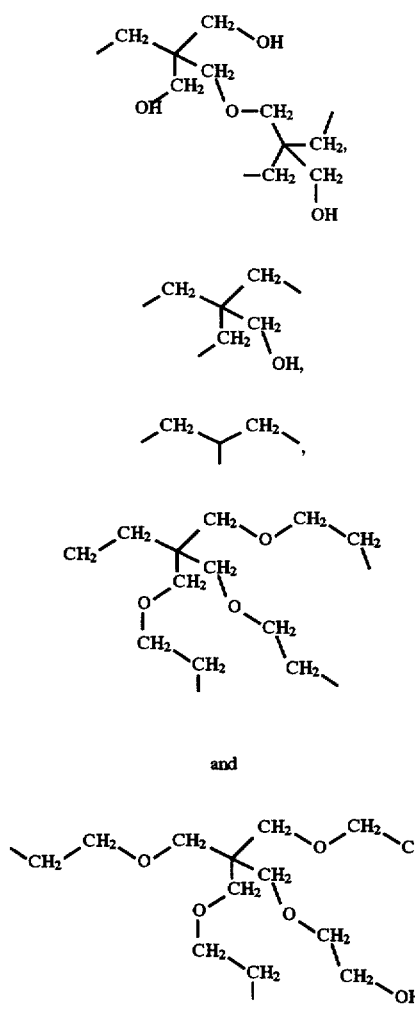
In detail, non-limiting examples of monomers (I) are shown in the following Table.
TABLE 1
| Monomers (I) |
| --- |
| No. |
| 1 |
| 2 |
TABLE 1-continued
| Monomers (I) |
| --- |
| No. |
| 3 |
| 4 |
| 5 |
| 6 |
| 7 |
| 8 |

TABLE 1-continued

Monomers (I)

| No. | |
|---|---|
| 9 | 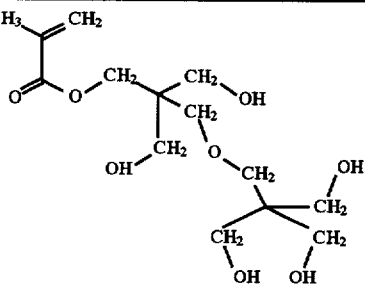 |
| 10 | 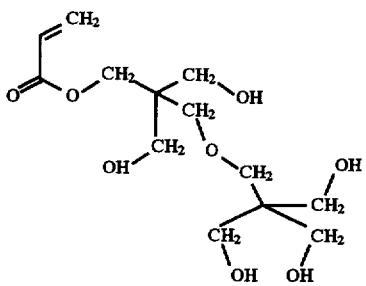 |

Examples of monomers (II), include monoanhydride chlorides and dianhydrides.

Preferred monoanhydride chlorides include the commercially available trimellitic acid derivative 1,2,4-benzene-tricarboxylic acid anhydride chloride; 1,2,3-benzene-tricarboxylic acid anhydride chloride; or the naphthalene-tricarboxylic acid derivatives, such as 1,2,6-, 2,3,6- and 1,4,5-naphthalene-tricarboxylic acid anhydride chloride.

Preferred dianhydrides include the commercially available compounds benzene-1,2,4,5-tetracarboxylic acid dianhydride (pyromellitic dianhydride) and naphthalene-1,4,5,8-tetracarboxylic acid dianhydride or naphthalene-2,3,6,7-tetracarboxylic acid dianhydride, respectively, which is formed simply through dehydration of the known naphthalene-2,3,6,7-tetracarboxylic acid.

The molar masses of the condensation products according to the present invention are between 300 and 10000 daltons, preferably between 500 and 7500 daltons, particularly preferred between 1000 and 5000 daltons, and can be determined through methods known to the expert such as vapor-pressure osmosis HPLC, SFC (Supercritical Fluid Chromatography).

The preparation of the oligomeric condensation products from aromatic carboxylic acid anhydrides or aromatic carboxylic acid anhydride chlorides and hydroxyalkyl(meth) acrylates, respectively, takes place advantageously through conversion of aromatic anhydride chlorides or dianhydrides with hydroxyalkyl(meth)acrylates. The monomers (I) and (II) can be used in differing as well as in equimolar stoichiometric ratios, which then correspondingly result in terminal anhydrides and hydroxides. Thus, a ratio of monomer 1 from Table 1 to 1,2,4-benzene-tricarboxylic acid anhydride chloride of greater than 1 to maximum 2 results in a condensation product with terminal anhydride groups (see the following formula (III)), which then can be saponified to carboxyl groups, whereas a ratio of these monomers of less than 1 to minimum 0.5 results in a condensation product with terminal hydroxyl groups (see the following formula (IV)).

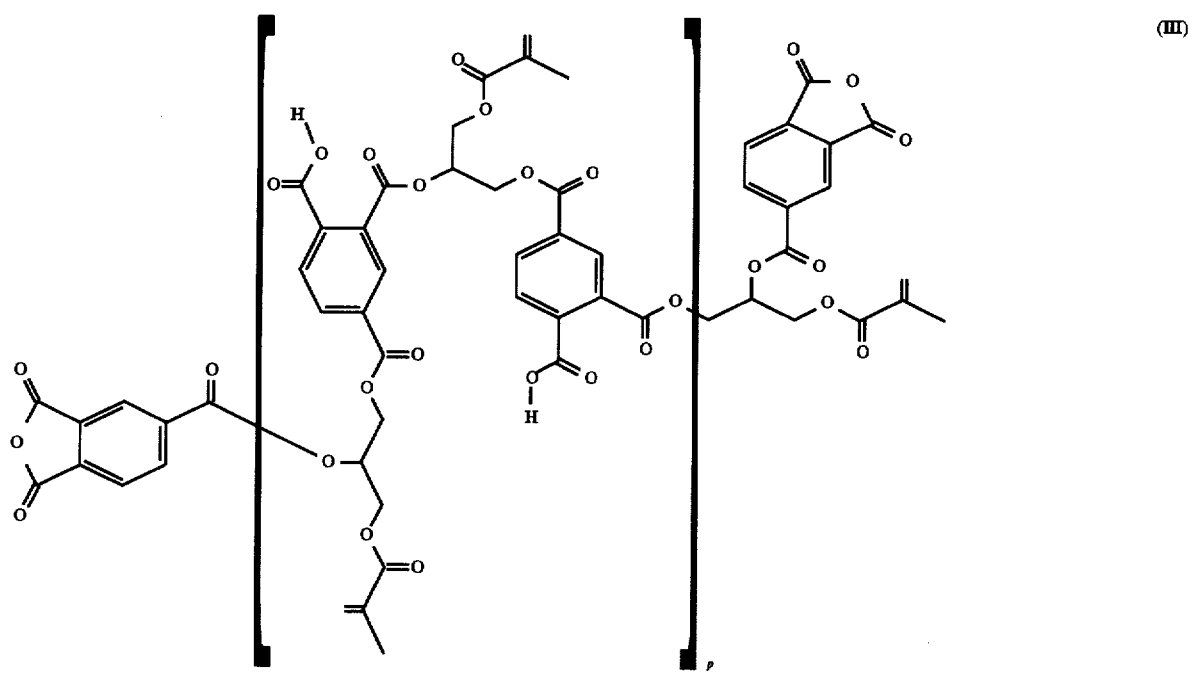

(III)

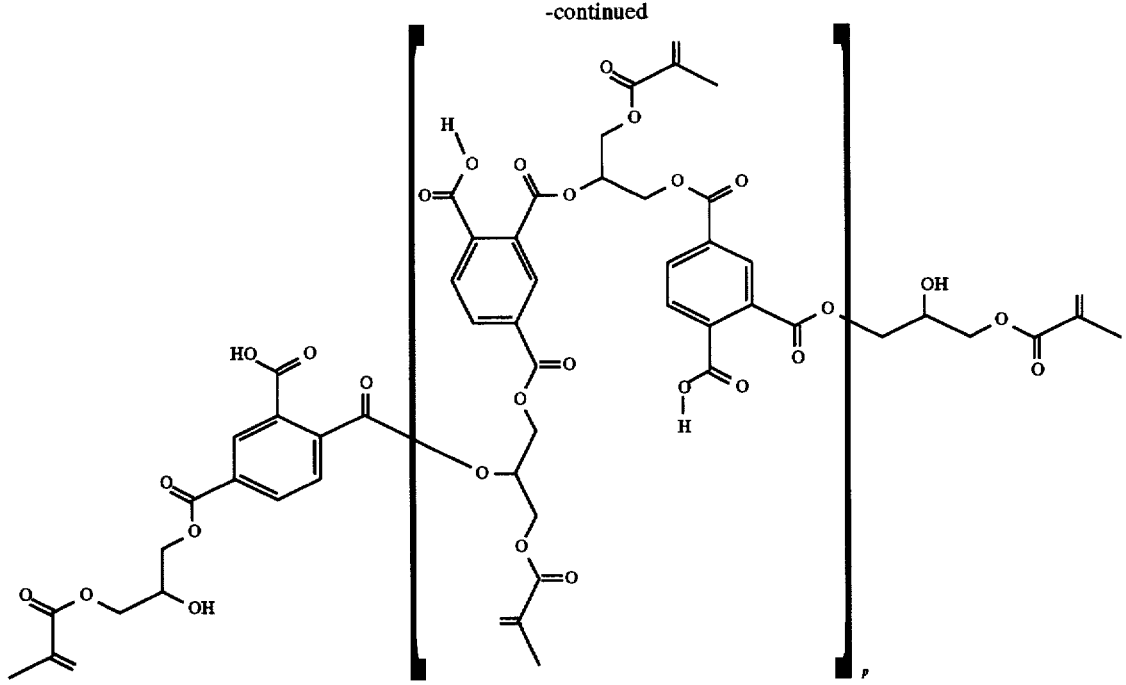

The repeating unit p is determined by the molar mass and ranges between 1 and 14 in the condensation products according to the invention.

Hydroxyl and anhydride groups form with precisely equimolar ratios, whereby the condensation and molar mass can be controlled by saponifying the anhydride during the reaction, for example; by adding water.

The hydroxyalkyl(meth)acrylates which form the basis of the oligomeric condensation products are partially available commercially or can be prepared in the known manner through esterification of polyhydroxyalkyl compounds with, for example; (meth)acrylic acid chloride.

The preparation of the condensation products according to the present invention preferably takes place in an organic solvent. Suitable organic solvents are aprotic solvents such as dioxane, tetrahydrofuran, N,N-dimethyl formamide, N,N-dimethyl acetamide, dimethyl sulphonamide, methyl ethyl ketone and acetone. More suitable are toluene and diethyl ether. Particularly preferred are xylene, dichloromethane, chloroform, methyl ethyl ketone and methyl-tert.-butyl ether.

A suitable temperature range for the preparation of the condensation products according to the present invention is between −30° and 110° C. It is preferred that the reaction be carried out between −10° and 50° C. and particularly preferred between −5° and 30° C. Additionally, inorganic or organic bases can be used for the preparation.

Preferred inorganic bases are the weak alkaline carbonates and hydrogencarbonates of sodium and potassium. Preferred organic bases are tert. amines, whereby triethylamine and pyridine are particularly preferred. The bases are used, with respect to the anhydrides or anhydride chlorides corresponding to formula (II) used, respectively, in 0.05- molar up to a quinquemolar quantity, whereby a dimolar to trimolar excess is preferred. The organic bases additionally act as solubilizer.

For the preparation of the condensation products according to the present invention, first the corresponding terminal hydroxides or anhydrides are formed. From the anhydrides, the dicarboxylic acids are available by means of hydrolysis.

The hydrolysis takes place at temperatures ranging between 0° and 100° C., preferably between 20° and 50° C. The hydrolysis can be performed subsequent to isolation of the anhydrides; however, a direct hydrolysis of the reaction batch, without isolating the anhydrides, is also possible. To perform the hydrolysis, water is added in an equimolar quantity, preferred, however, is in excess of a decamolar quantity. The hydrolysis can be catalyzed through the targeted addition of acids, especially sulfuric acid, phosphoric acid, toluenesulphonic acid or acid ion exchangers, or through the addition of bases, such as sodium and potassium hydroxide, sodium and potassium carbonate or sodium and potassium hydrogencarbonate, respectively.

The reactivity of compounds curable through polymerization can be precisely described through the photo-DSC method (Differential Scanning Calorimetry).

In this method, photoactivated samples are irradiated in a DSC apparatus with a high-intensity irradiation source, for example, a halogen lamp with heat protection filter. The heat flow is recorded under irradiation as a function of time. As a reference, samples with the same composition without a photo-initiator are used. For evaluation purposes, the t-max value can be determined as a measurement of the reaction rate. t-max is the time from initiation of the irradiation to obtaining of the reaction maximum (maximum heat flow); the smaller the t-max, the greater the photo-reactivity.

The formulations according to the present invention contain, aside from the new condensation products, solvents, initiators, co-activators and, optionally, additional (meth) acrylic acid esters as co-monomers. In particular, mixtures of a variety of condensation products can also be used in the formulations according to the invention.

The solvents of the formulations must dissolve the components and, if the formulation is for dental purposes, must be non-toxic. Preferred are water and volatile organic solvents such as methanol, ethanol, propyl alcohol, isopropyl alcohol, acetone, methyl ethyl ketone, methyl acetate and ethyl acetate and tetrahydrofuran. Generally, one uses 10 to 1000 parts by weight, preferably 50 to 300 parts by weight, of the solvent, with respect to the condensation products.

Mixtures of these solvents may also be particularly preferred, whereby aqueous mixtures are most particularly preferred.

Initiators within the framework of the present invention include radical formers which initiate a radical polymerization. Preferred are photo-initiators which initiate a radical polymerization when exposed to light, for example, UV light, visible light or laser light.

These so-called photo-polymerization initiators are generally known from the literature. Preferably, they are mono- or dicarbonyl compounds such as benzophenone, benzoin and its derivatives, in particular benzoin methyl ether, benzil and benzil derivatives, and other dicarbonyl compounds such as diacetyl, 2,3-pentanedione and α-diketo derivatives of norbornane and substituted norbornanes, metal carbonyls, such as pentacarbonyl manganese, or quinones, such as 9,10-phenanthrenequinone and naphthoquinone. Especially preferred is camphorquinone.

The formulations according to the present invention generally contain 0.01 to 2% by weight, preferably 0.1 to 0.5% by weight, of an initiator, with respect to the quantity of polymerizable compounds.

If one of the compound components in contact with the formulation according to the present invention already contains an initiator of the described type, one may omit the initiator in the formulation.

It can be advantageous to add co-activators to the formulations according to the present invention, which accelerate the polymerization reaction. Known accelerators are, for example, amines such as p-toluidine, dimethyl-p-toluidine, trialkylamines such as trihexylamine, polyamines such as N,N,N',N'-tetraalkylenediamines, barbituric acid and dialkyl barbituric acids. Dimethylamino benzene-sulphonamides as described in DE-A 31 35 113 are particularly preferred.

Co-activators are generally used in a quantity of 0.02 to 4% by weight, preferred is 0.2 to 1% by weight, with respect to the quantity of polymerizable compounds.

Other suitable components for the formulations according to the invention are (meth)acrylic esters as co-monomers. Preferred are esters of (meth)acrylic acid with mono- to pentahydric alcohols with 2 to 30 carbon atoms. Epoxide (meth)acrylates and urethane (meth)acrylates are particularly preferred.

Also useful are tricyclodecane derivatives (EP-A 0 023 686) and reaction products from polyols, diisocyanates and hydroxyalkylmethacrylates (DE-A 37 03 120, DE-A 37 03 080 and DE-A 37 03 130).

Particularly preferred as the (meth)acrylic acid ester is the so-called Bis-GMA having the following formula:

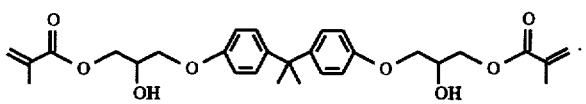

Of course, it is possible to use mixtures of the various (meth)acrylic acid esters, for example, mixtures of 20 to 70 parts by weight of Bis-GMA and 30 to 80 parts by weight of triethylene glycol di(meth)acrylate.

Furthermore, the formulations according to the present invention can contain up to 10 parts by weight of standard additives, such as stabilizers, inhibitors and light-protective agents.

The formulations according to the present invention can be prepared by mixing through intensive stirring the condensation products, solvent, initiator and, optionally, additional components.

The formulations according to the present invention are preferably used as adhesives, particularly for improving adhesion of polymerizable dental materials to the hard substance of the tooth enamel and collagen-containing dentine.

In a special embodiment, prior to treatment with the formulations according to the present invention, the collagen-containing hard substance of a tooth is conditioned with a fluid which has a pH value in the range of 0.1 to 3.5. This conditioning fluid generally contains acids with a $pK_a$ value less than 5 and, optionally, an amphoteric amino compound with a $pK_a$ value in the range of 9.0 to 10.6 and a $pK_b$ value in the range of 11.5 to 12.5. The following acids, for example, can be contained in the conditioning fluid: phosphoric acid, nitric acid, pyruvic acid, citric acid, oxalic acid, ethylenediaminetetraacetic acid, acetic acid, tartaric acid, and malic acid. Furthermore, the conditioning fluid can contain substances from the group of polyethylene glycols and metal hydroxides. In particular, the above listed polybasic acids can also be used in the form of partial metallic salts, as long as free acid functions remain.

Use of the formulations according to the present invention can be carried out, for example, as follows:

When performing dental restoration, after mechanically cleaning the collagen-containing hard substance of a tooth, one first applies the conditioning fluid with a small amount of cotton wool, allows it to act for a short period of time (for example, 60 seconds), rinses the tooth substance with water and dries it with an air flow. Thereafter, one applies the formulation according to the present invention in one thin layer with, for example, a small brush, and dries it with an air flow. After the treatment the actual filling material is applied, for example, a synthetic filling material standard in the dental field.

Aside from their use in formulations suitable as adhesives, the condensation products according to the present invention can also be used advantageously as mixing fluids for glass-ionomer cements and in bone cements.

EXAMPLES

Examples 1-3

Preparation of Oligomeric Condensation Products According to the Present Invention Example 1

Preparation of Condensation Product 1

Into a solution of 210.57 g (1,000 mole) of 1,2,4-benzenetricarboxylic acid anhydride chloride in 650 ml dry methyl ethyl ketone and 202.38 g (2,000 mole) dry triethylamine, a solution of 160.2 g (1,000 mole) of glycerol monomethacrylate (monomer 1 from Table 1) in 250 ml dry methyl ethyl ketone was dripped at −5° C. while stirring. After stirring for 16 hours at ambient temperature, the precipitated light-colored solid matter was suction-filtered, the filtrate extracted aqueously and dried.

The obtained methyl ethyl ketone solution contained the desired condensation product and could be used directly for the hydrolysis of the remaining anhydride groups. For this, 50 ml de-ionized water was added to the solution which was stirred at ambient temperature for a period of 16 hours.

After addition of 200 mg 2,6-di-tert.-butyl cresol the obtained solution could be concentrated to 327.7 g (87% of the theoretical amount) of a yellowish, viscous oil.

IR:=3400, 2300, 2900, 2600, 2400, 1720, 1640, 1500, 1440, 1420, 1380, 1295, 1240, 1175, 1125, 1075, 1020, 950, 865, 825, 760 cm$^{-1}$. $^1$H-NMR (CDCl$_3$, 200 MHz):=8.55–7.8 (3H); 6.2 and 5.6 (each 1H); (1H); 4.9–4.2 (4H); 1.9 (3H) ppm; Molar mass (HPLC): 1100 daltons.

Example 2

Preparation of Condensation Product 2

A solution of 160.2 g (1 mole) glycerol monomethacrylate in 250 ml methyl ethyl ketone was added at room temperature, while stirring, to a mixture of 218.12 g (1 mole) pyromellitic dianhydride, 222.2 g (2.2 mole) triethylamine and 2200 ml methyl ethyl ketone and heated to 50° C. for 3 hours. The crude batch was filtrated, the filtrate was poured into ice water, acidified with semi-concentrated sulfuric acid for the hydrolysis and stirred for 30 minutes. The two phases were separated; the organic phase was washed once more with water and dried over sodium sulphate.

IR:=3400, 2900, 2600, 2400, 1720, 1640, 1500, 1420, 1380, 1295, 1250, 1175, 1110, 1020, 950, 825, 770 cm$^{-1}$. $^1$H-NMR (acetone-d$_6$, 200 MHz):=8.35–8.0 (2H); 6.1 and 5.6 (each 1H); 5.8 (1H); 4.7–4.2 (5H); 1.9 (2H) ppm.

Example 3

Preparation of Condensation Product 3

A solution of 160.2 g (1 mole) glycerol monomethacrylate in 250 ml methyl ethyl ketone was added at room temperature, while stirring, to a mixture of 268.18 g (1 mole) naphthalene-1,4,5,8-tetracarboxylic dianhydride, 222.2 g (2.2 mole) triethylamine and 2200 ml methyl ethyl ketone and heated to 50° C. for 3 hours. The crude batch was filtrated, the filtrate was poured into ice water, acidified with semi-concentrated sulfuric acid for hydrolysis and stirred for 30 minutes. The two phases were separated; the organic phase was washed once more with water and dried over sodium sulphate.

IR:=3300, 3050, 2900, 2650, 2500, 1775, 1710, 1630, 1595, 1560, 1540, 1515, 1456, 1440, 1380, 1330, 1300, 1225, 1160, 1125, 1100, 1040, 950, 880, 820, 765, 700 cm$^{-1}$.

Example 4

Testing of the Photo-reactivity With the Aid of the Photo-DSC Method

The following components were intensively mixed with each other:
(a) Present Invention
5.0 g Condensation product according to Example 1
10 mg Camphorquinone
25 mg p-dimethylaminobenzenesulphonic acid-N,N-diallyl amide (DASA)
(b) Comparison
5.0 g 4-MET
10 mg Camphorquinone
25 mg p-dimethylaminobenzenesulphonic acid-N,N-diallyl amide (DASA)

Camphorquinone and p-dimethylaminobenzenesulphonic acid-N,N-diallyl amide form the photo-initiator system.

The samples were irradiated at 30° C. in a DSC apparatus with a halogen lamp (75 W) with a heat protection filter. The heat flow was recorded under irradiation as a function of time. As a reference, samples with the same composition without a photo-initiator were used. During the test, rinsing with nitrogen took place. For the evaluation, the t-max value was determined as a measurement of the reaction rate. t-max is the time from initiation of the irradiation to obtaining of the reaction maximum (maximum heat flow); the smaller the t-max, the larger the photo-reactivity.

Example 5

Inhibition of the Polymerization Through Oxygen

To test the inhibition sensitivity of monomers, the thickness of the non-polymerized surface layer of samples which were irradiated with light in accordance to Example 4 is determined.

Cylindrical molds (diameter of 6 mm, depth of 0.5 mm), which were drilled into a rectangular brass plate, are filled in three layers with the monomer to be tested and, after evaporating the solvent, irradiated with the Translux CL (Heraeus Kulzer GmbH, Hanau, Germany) light device for a duration of 20 seconds at ambient atmosphere and dusted with a very small amount of colloidal silver powder. The brass plate is then placed on the stage of a reflected-light microscope against a rectangular frame support. The stage position can be adjusted with the aid of two servo-motors in the x and y directions with a reproducibility of±1 μm. With a constant y position, the height coordinates z are then determined at a distance of 1 mm along the x axis with the depth-of-field method. The z-value determination is carried out by means of a displacement pickup which is attached to the stage vertical to the stage plane and which indicates the height adjustment in micrometer units by means of a calibrated voltmeter. The reproducibility of the z-value determination is±1 μm. Immediately subsequent to determination of the initial value, the sample surface is carefully washed with ethanol. The mold is then returned to the microscope stage and, after entering the x/y starting positions, the z values are again determined. The differences between the first and second measurements are recorded as a mean value per sample and correspond to the surface layer which is not polymerized due to the inhibition through oxygen. Three samples are prepared and measured per monomer.

The smaller the thickness of the non-polymerized surface layer (inhibition layer), the smaller the inhibition through oxygen, the better the curing and thus the mechanical resistance of the polymerizate and the entire system to be cemented.

Results
Non-polymerized surface layer (Am)
Condensation product according to example 1 1.3±0.8
4-MET (comparative test) totally washable, that is, no curing.
Only the compound according to the invention demonstrates curing with a very small inhibition layer.

Examples 6 and 7

Preparation of Formulations for Use as Adhesives

The formulations were prepared by intensively mixing the components listed in the examples.

Example 6 (Present Invention)

5 g Acetone
2.5 g Condensation product according to Example 1
2.5 g Hydroxyethylmethacrylate
0.01 g Camphorquinone
0.025 g DASA

Example 7 (Comparative Test)

5 g Acetone
5 g 4-MET 0.01 g Camphorquinone
0.025 g DASA

The effectiveness of the adhesives was tested by determining the shear bonding strengths with respect to enamel and dentine and by performing a microscopic edge analysis on cylindrical dentine cavities which were filled with a conventional composite filling material (Pekafill, Heraeus Kulzer GmbH, Hanau, Germany) subsequent to conditioning of the dentine and application of the adhesive. Human teeth were used which had been preserved in 1 wt. % chloramine solution for a maximum of three months after extraction. Prior to their use in the test and after a careful cleaning under running water, the teeth were stored in a physiological salt solution for a minimum of three but a maximum of ten days.

Shear Bonding Strength

On the day before their use in the bonding test, the teeth, lying on an approximal side, are individually embedded with epoxy resin (Lekutherm® X20, curing agent T3, Bayer AG, Leverkusen, Germany) in cylindrical rubber molds having a diameter of 25 mm and a height of 12 mm. The teeth are ground by means of wet-grinding with SiC papers coarseness values of 240, 320, 400 and 600, to the extent that a sufficiently large enamel surface or a peripheral dentine surface is exposed to allow bonding to it a synthetic cylinder with a diameter of 3.5 mm. Subsequent to rinsing with de-ionized water and drying with an air flow, the conditioning gel Gluma CPS (20 wt. % $H_3PO_4$) (Heraeus Kulzer GmbH, Hanau, Germany) is applied and carefully rinsed off with a spray of water after 30 seconds. The conditioned tooth surface is then exposed to a weak air flow for a very limited period of time only in order to remove the water from the surface (wet technique!). A thin layer of adhesive is applied with a brush and the solvent is evaporated by carefully blowing it off with compressed air. The application and evaporation is repeated twice prior to irradiation with the Translux CL light device for a duration of 20 seconds. The test sample pretreated in this manner is then clamped with a clamping device under a double-part cylindrical teflon mold (diameter of 3.5 mm, height of 1 mm) The filling material is applied with a syringe, the mold filled with excess covered with a transparent strip and, finally, irradiated with the Translux CL light device for a duration of 60 seconds. Immediately afterwards, the "TEFLON" mold is removed and the test sample stored in 37° C. warm water for a period of 24 hours until initiation of the shearing stress. For that, the cylindrical test sample is stressed in a universal testing machine with the aid of a force piece parallel and very close to the around tooth surface, at a speed of 1 mm/minute, until the cylinder separates from the tooth. The shear bonding strength is the quotient of the breaking strength and the bonding surface and is indicated in MPa. The localization of the fracture is inspected under the stereomicroscope (magnification 60×) and described as adhesive or cohesive failure.

Results
Shear bonding strength to dentine (MPa)
Formulation according to Example 6 14.7±1.3
Formulation according to Example 7 7.2±0.9
(Comparative test)

Solely with the formulation according to the present invention from Example 6 was the fracture situated interfacially adjacent in the synthetic material (cohesive failure). The formulation from Example 7 (comparative test) exhibited adhesive failure.

Shear bonding strength to enamel (MPa)
Formulation according to Example 6 17.6±3.3
Formulation according to Example 7 8.3±2.4
(Comparative test)

Solely with the formulation according to the present invention from Example 6 was the fracture situated deep in the enamel. The formulation from Example 7 (comparative test) exhibited adhesive failure.

This confirms that in the case of using only formulations according to the present invention is the bond between the substrates stronger than the cohesive strength of the synthetic material or enamel. This confirms the favorable performance of the formulations according to the present invention used as an adhesive.

Microscopic Edge Analysis

To determine the cavity edge adaptation, extracted premolars or molars are ground on their approximal side by means of wet-grinding with SiC paper with a coarseness of 600 to the extent that a sufficiently large dentine surface is exposed in which a cylindrical cavity (diameter of 3 mm, depth of approximately 1.5 mm) can be prepared. The cavity is form-finished using a medium-coarse diamond instrument with the aid of a high-speed dental angle implement under water-cooling. After careful cleaning with water, conditioning and application of the adhesive/adhesion promoter takes place as described above prior to putting in the composite material Pekafill, covering with a strip and irradiation with the Translux CL light for a duration of 60 seconds. Immediately after polymerization, the teeth are stored in water for 10–15 minutes at ambient temperature, prior to removing the excess filling material through careful wet-grinding with SiC paper with coarseness values of 600 and 4000 and exposing of the cavity edge. Subsequently, an inspection of the cavity edge is performed under a reflected-light microscope at 500-fold magnification. If a separation of the filling material has occurred, the maximum gap width is determined with the aid of a screw-type micrometer eyepiece and indicated in µm. The microscopic inspection is performed within a maximum of five minutes before gaps can occur due to drying.

Results

The formulation according to the invention from Example 6 was determined to be extremely effective. No gap was found, the cavity edge adaptation was perfect. The bonding to dentine took place via a hybrid layer formation which, corresponding to the preceding conditioning, has a layer thickness of 10–14 µm. In contrast thereto, the comparison with the formulation from Example 7 showed separation of the filling material with a gap of 7 µm.

What is claimed is:

1. An oligomeric condensation product prepared from glycerol monomethacrylate of the formula

$$CH_2=C(CH_3)COOCH_2CH(OH)CH_2OH \qquad (I)$$

and 1,2,4-benzene-tricarboxylic acid anhydride chloride of the formula

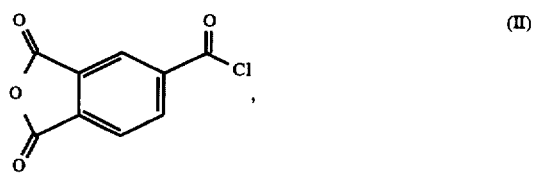

(II)

wherein said oligomeric condensation product is of a formula selected from the group consisting of (A) a formula (III) with anhydride groups

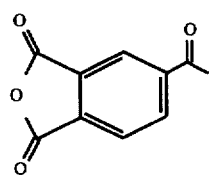

(III)

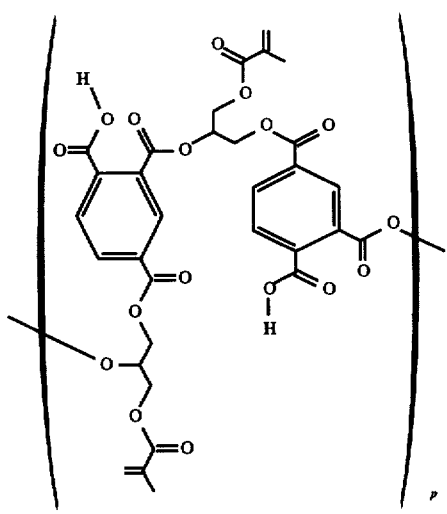

when (I) to (II) is in a ratio of greater than 1 to a maximum of 2, and p is 1 to 14, and (B) a formula (IV) with hydroxy groups (IV)

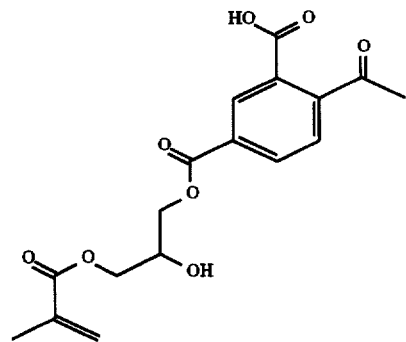

-continued

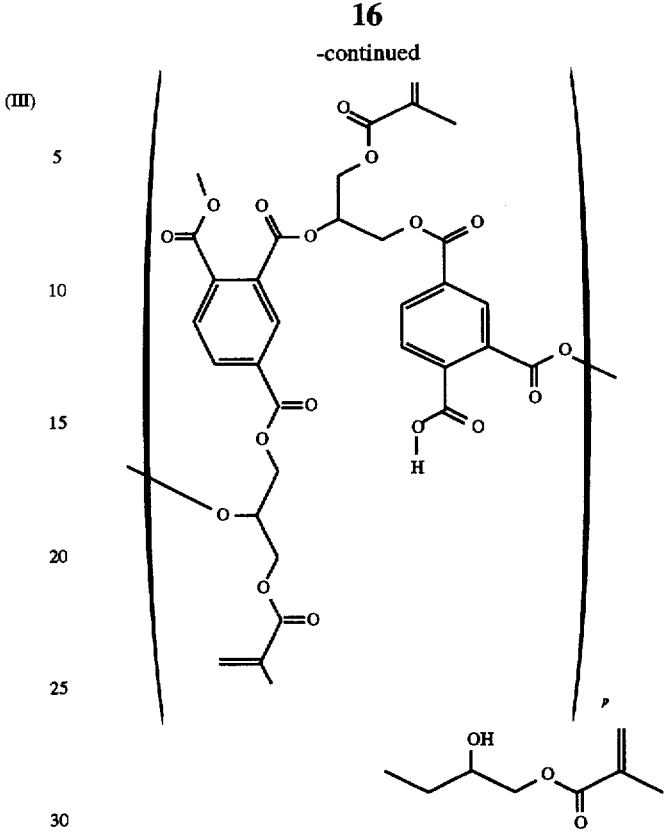

when (I) to (II) is in a ratio of less than 1 to a minimum of 0.5, and p is 1 to 14.

2. A formulation comprising an effective adhesive amount of the condensation product of claim 1 and at least one additional component selected from the group consisting of a solvent, an initiator, a co-activator, a co-monomer, a stabilizer, an inhibitor and a light-protective agent.

3. The formulation according to claim 2, which contains an initiator for initiating a radical polymerization, the initiator being a monocarbonyl compound or dicarbonyl compound.

4. A method for improving the adhesion of a polymerizable dental filling material to the enamel or the collagen-containing dentine of a tooth, comprising contacting the tooth with an effective adhesive improving amount of the condensation product according to claim 1.

5. A method of improving adhesion of a polymerizable dental filling material to the collagen-containing dentine of a tooth comprising contacting a tooth with a fluid having a pH value of 0.1 to 3.5, the fluid containing at least one acid with a $pK_a$ value of less than 5 and optionally an amphoteric amino compound with a $pK_a$ value of 9.0 to 10.6 and a $pK_b$ value of 11.5 to 12.5 and then contacting the tooth with an effective adhesive improving amount of the condensation product according to claim 1.

6. In a mixing fluid for a glass-ionomer cement, the improvement comprising the mixing fluid containing the condensation product according to claim 1.

7. In a bone cement, the improvement comprising the bone cement containing the condensation product according to claim 1.

* * * * *